US006432638B2

(12) United States Patent
Dervan et al.

(10) Patent No.: US 6,432,638 B2
(45) Date of Patent: *Aug. 13, 2002

(54) TRIPLE HELIX RECOGNITION OF DNA

(75) Inventors: Peter B. Dervan, Pasadena; Heinz E. Moser, S. Pasadena, both of CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/128,732

(22) Filed: Aug. 4, 1998

Related U.S. Application Data

(60) Continuation of application No. 08/152,250, filed on Nov. 12, 1993, now Pat. No. 5,789,155, which is a continuation of application No. 07/614,205, filed on Nov. 16, 1990, now abandoned, which is a division of application No. 07/115,922, filed on Oct. 30, 1987, now abandoned.

(51) Int. Cl.[7] ............................ C12Q 1/68; C07H 21/04
(52) U.S. Cl. .................. 435/6; 536/23.1; 536/24.1; 536/24.3; 536/24.32; 536/24.33; 536/25.3; 435/325; 435/455
(58) Field of Search ............................. 435/375, 6, 29, 435/325, 455; 514/44; 536/24.5, 23.1, 24.3, 24.31, 24.32, 24.1, 25.3

(56) References Cited

U.S. PATENT DOCUMENTS

| 4,358,535 A | 11/1982 | Falkow et al. ................ 435/5 |
| 4,563,417 A | 1/1986 | Albarella et al. .............. 435/6 |
| 4,599,303 A | 7/1986 | Yabusaki et al. .............. 435/6 |
| 4,665,184 A | 5/1987 | Dervan et al. ............... 546/109 |
| 4,711,955 A | 12/1987 | Ward et al. .................... 536/29 |
| 4,795,700 A | 1/1989 | Dervan et al. ................ 439/5 |
| 4,828,979 A | 5/1989 | Klevan et al. ................. 435/6 |
| 4,835,263 A | 5/1989 | Nguyen et al. ............... 536/27 |
| 4,837,312 A | 6/1989 | Dervan et al. ............... 536/27 |
| 5,422,251 A | 6/1995 | Fresco ....................... 435/91.1 |
| 5,789,155 A * | 8/1998 | Dervan et al. ................ 435/6 |
| 5,874,555 A * | 2/1999 | Dervan et al. ............. 536/23.1 |

FOREIGN PATENT DOCUMENTS

| EP | 117777 | 9/1984 |
| EP | 169787 | 1/1986 |
| EP | 214908 | 3/1987 |
| WO | 8804301 | 6/1988 |

OTHER PUBLICATIONS

Antisense '97: A roundtable on the state of the industry. Nature Biotechnol. 15: 519–524, Jun. 1997.*
Gewirtz et al. Facilitating oligonucleotide delivery: Helping antisense deliver on its promise. Proc. Natl. Acad. Sci. USA 93: 3161–6163, Apr. 1996.*
Gura. Antisense has growing pains. Science 270: 575–577, Oct. 1995.*
Rojanasakul. Antisense oligonucleotide therapeutics: Drug delivery and targeting. Adv. Drug Delivery Rev. 18: 115–131, 1996.*
Stull et al. Antigene, ribozyme and aptamer nucleic acid drugs: Progress and prospects. Pharm. Res. 12: 465–483, Apr. 1995.*
Taylor et al., *Tetrahedron*, 40:457–465 (1984).
Schultz et al., *PNAS*, 80:6834–6837 (1983).
Dreyer et al., *PNAS*, 82:968–972 (1985).
Van Dyke et al., *Science*, 225:1122–1127 (1984).
Hertzberg et al., *J. Am. Chem. Soc.*, 104:313–315 (1982).
Zerial et al., *Nucleic Acids Research*, 15:9909–9919 (1987).
Cazenabe et al., *Nucleic Acids Research*, 15:10507–10521 (1987).
LeDoan et al., *Nucleic Acids Research*, 15:7749–7760 (1987).
Broitman et al., *PNAS*, 84:5120–5124 (1987).
Lipsett et al., *J. Biiol. Chem.*, 239:1256–1260 (1964).
Marck et al., *Nucleic Acids Research*, 5:1017–1028 (1978).
Torrence et al., *Biochemistry*, 15:724–734 (1976).
Perlgut et al., *Nature*, 254:86–87 (1975).
Chu et al., PNAS, 82:963–967 (1985).
Hertzberg et al., *Biochemistry*, 23:3934–3945 (1988).
Morgan et al., *J. Mol. Biol.*, 37:63–80 (1968).
De Clercq et al., *J. Biol. Chem.*, 250:2521–2531 (1975).
Lipsett, *J. Biol. Chem.*, 239:1256–1260 (1964).

* cited by examiner

Primary Examiner—John L. LeGuyader
Assistant Examiner—Janet Epps
(74) *Attorney, Agent, or Firm*—Richard F. Trecartin; Dorsey & Whitney LLP

(57) ABSTRACT

Probes and processes for their use for specific recognition and/or cleavage of double-stranded DNA or RNA at sequence specific desired loci through the intermediacy of a triple helix are disclosed. These probes may also be used as diagnostic chemotherapeutic agents through incorporation of a radiolabeled, fluorescing, or otherwise detectable molecule. Preferred assay conditions are also provided for recognition of homopurine-homopyrimidine double-helical tracts within large DNA by triple helix formation under physiological conditions. Hybridization probes for double-stranded recognition with binding site sizes that range >8 base pairs are also provided.

20 Claims, 7 Drawing Sheets

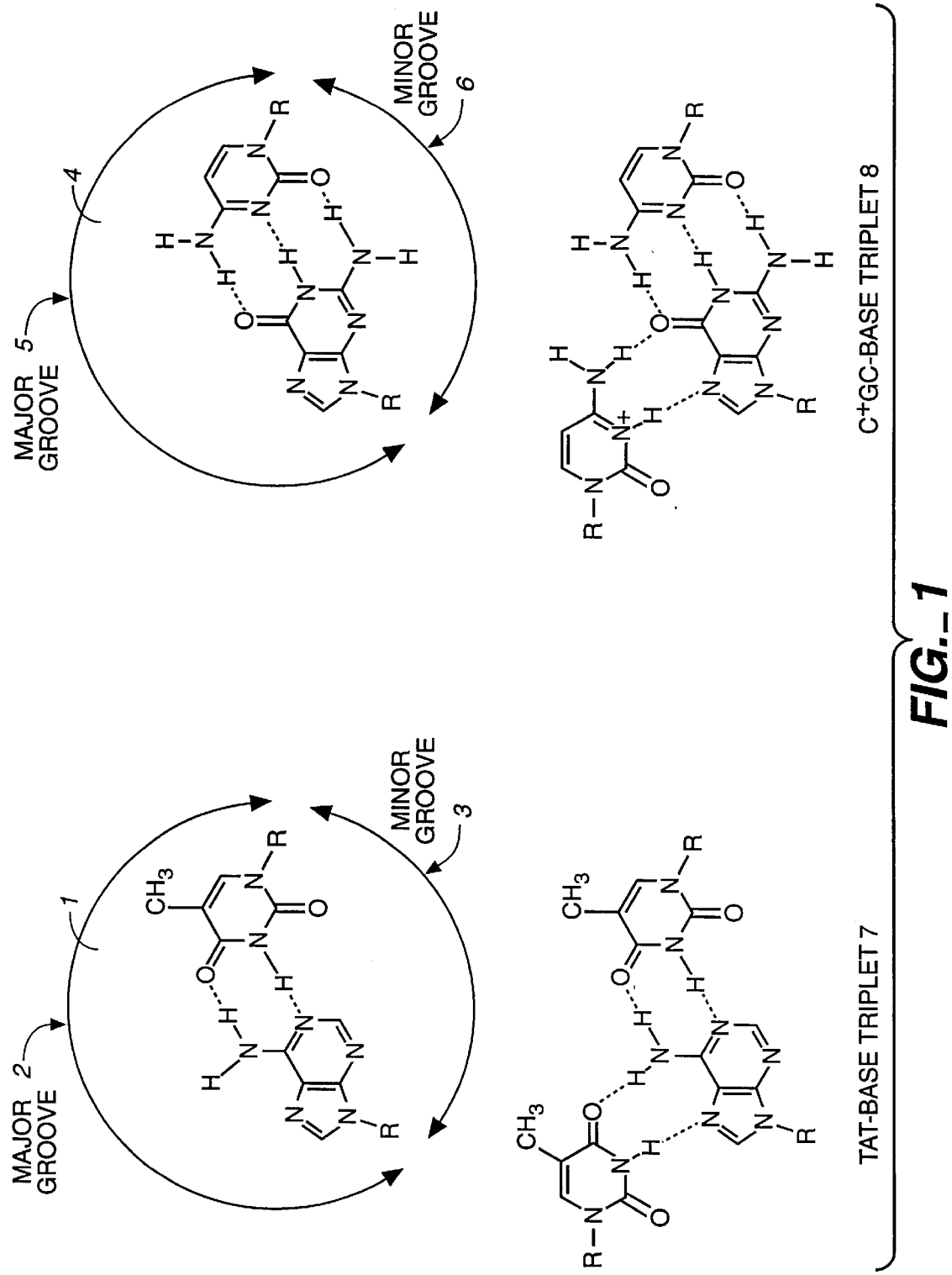
FIG._1

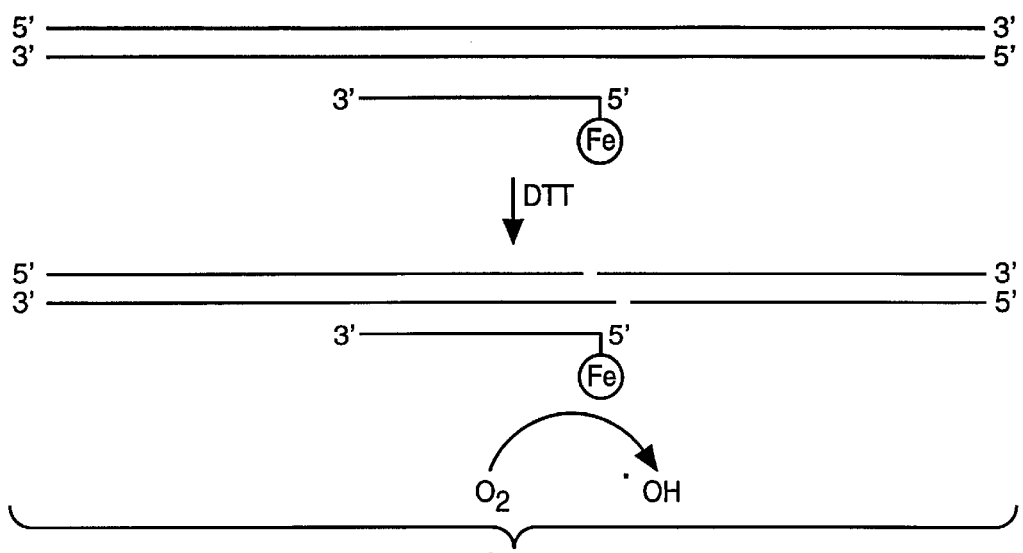
FIG._2
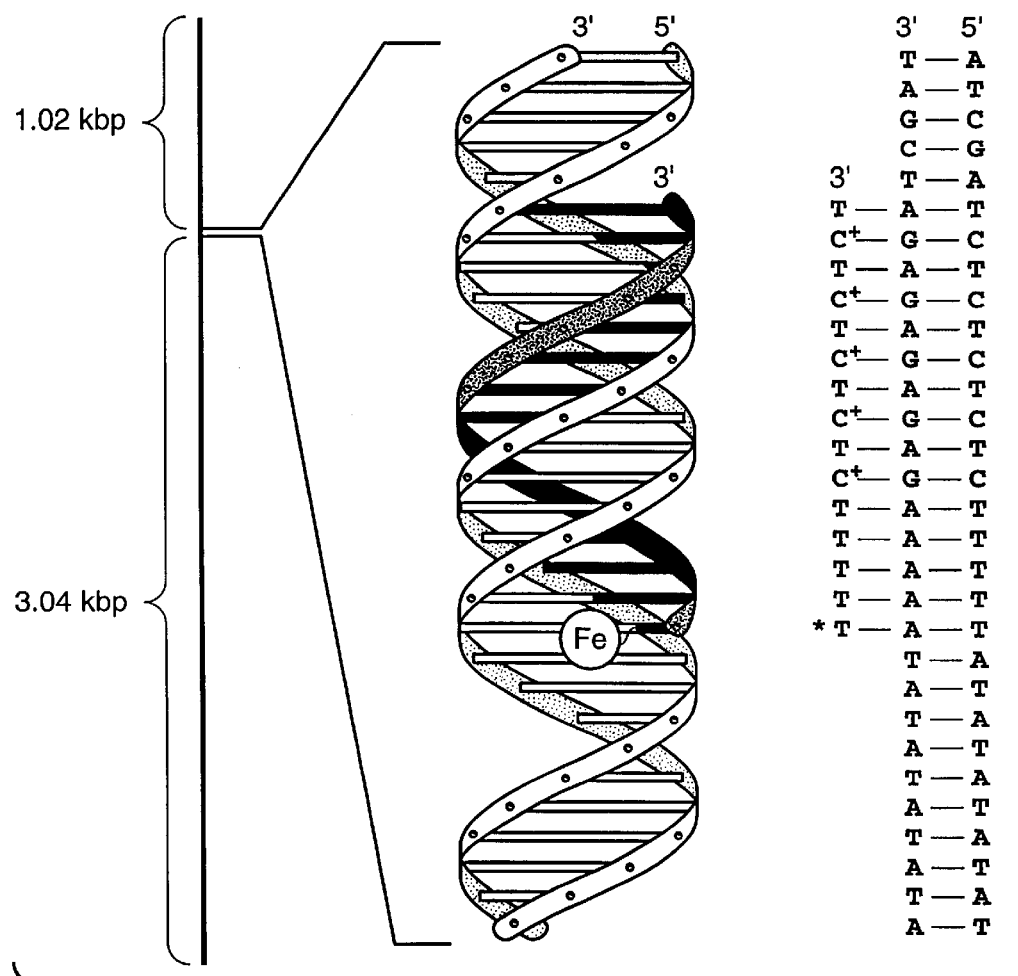
FIG._6B

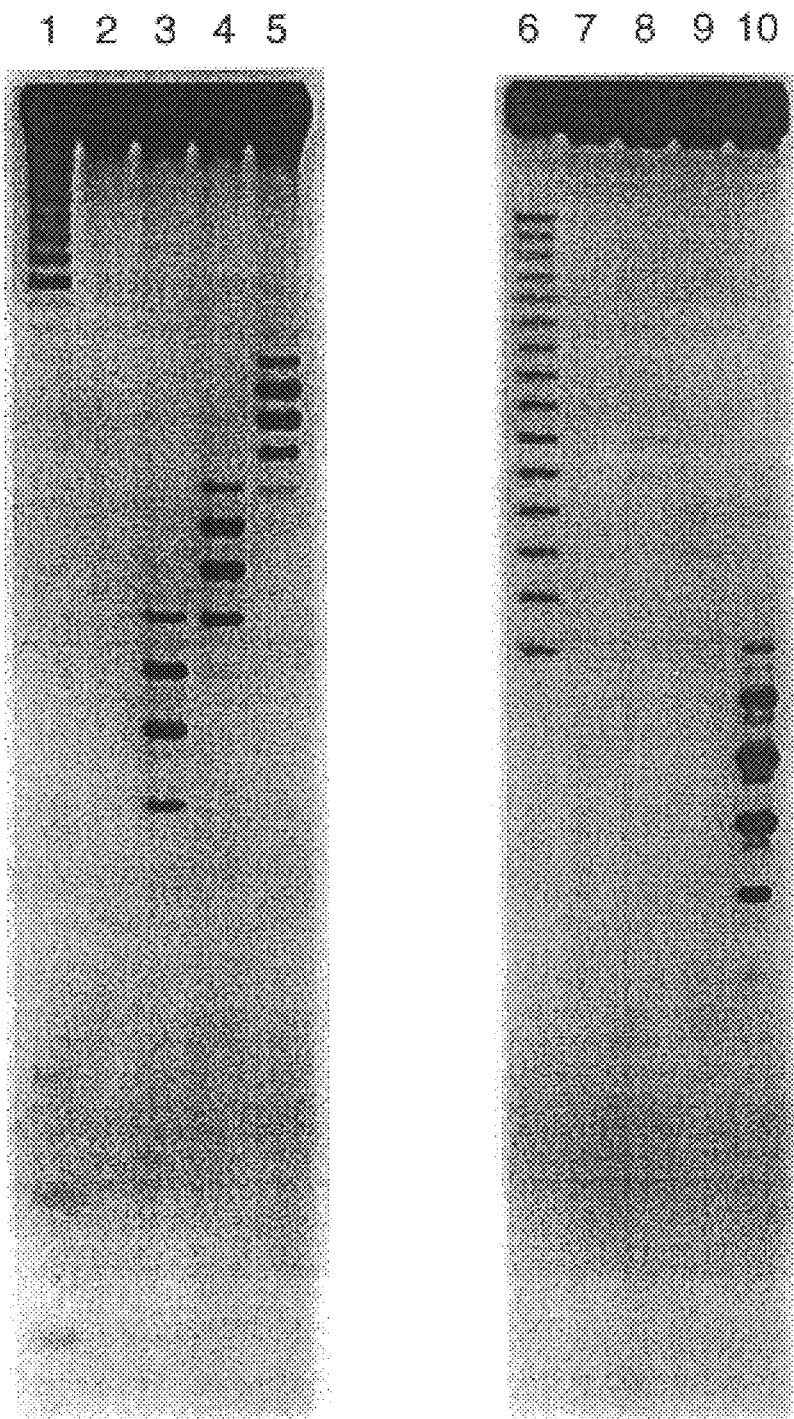
FIG._3A

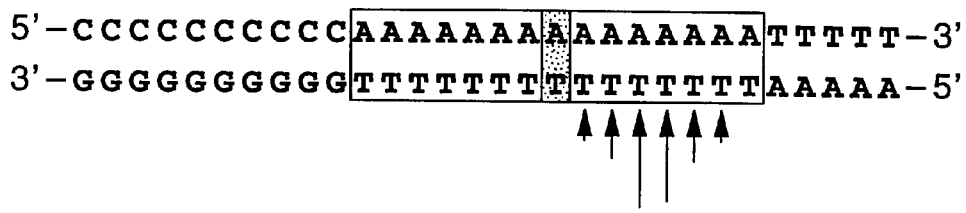
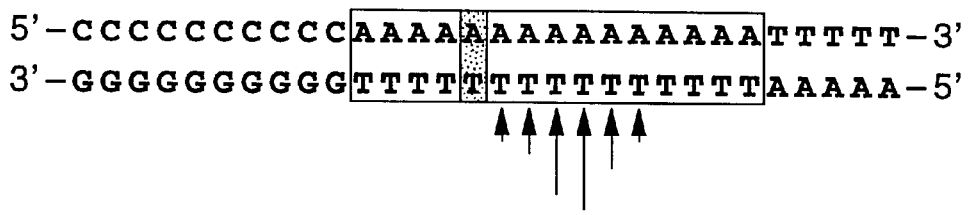
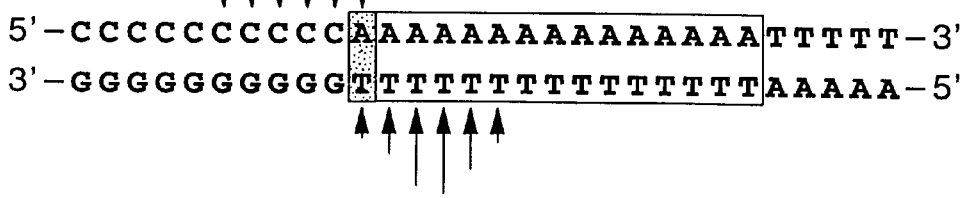
FIG._3B

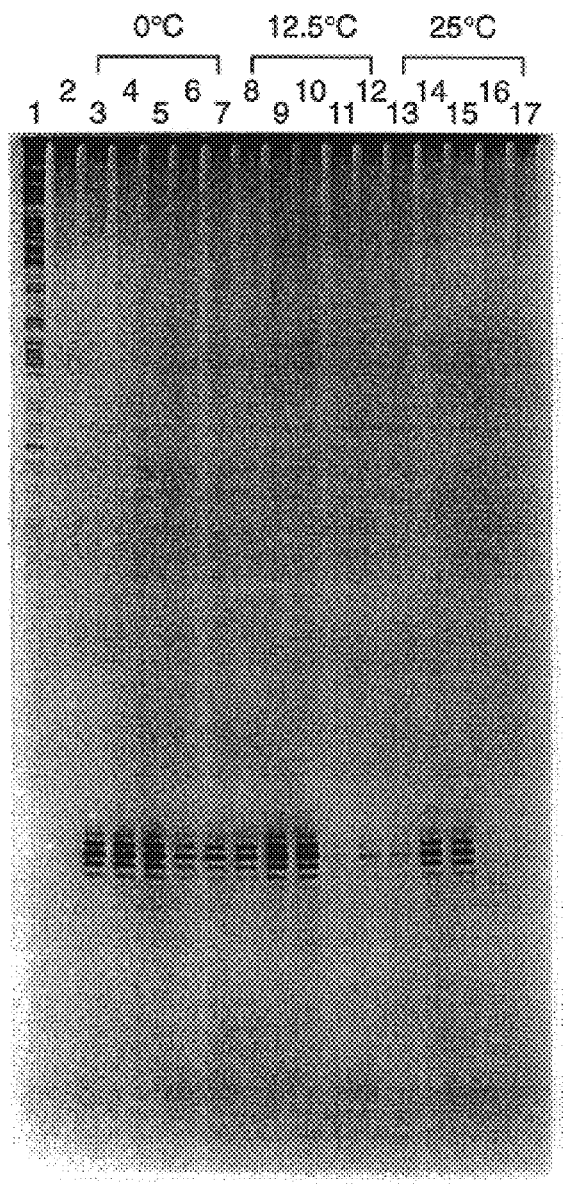
FIG._4A
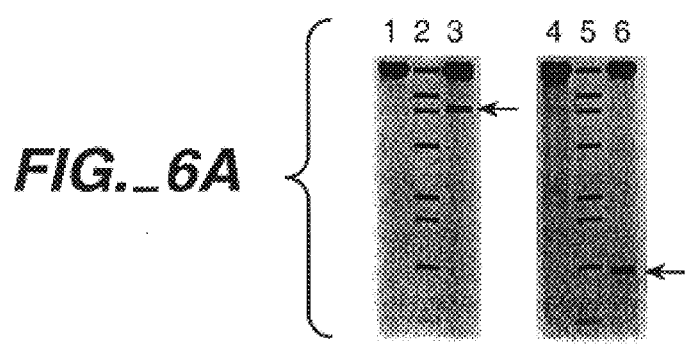
FIG._6A

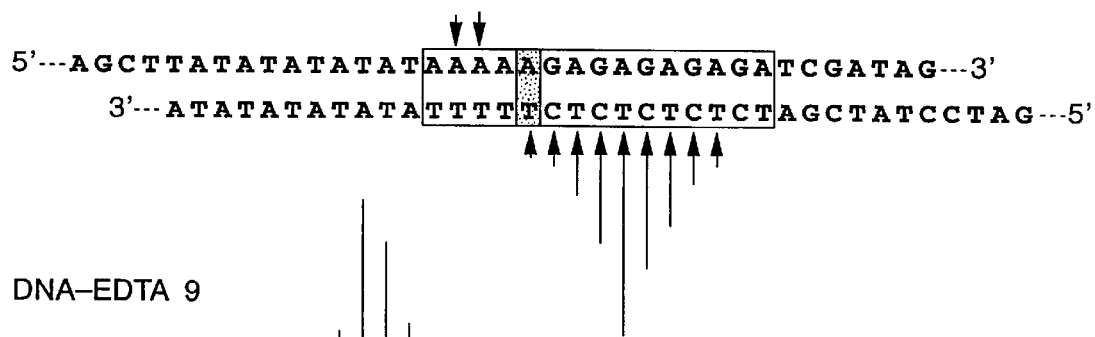
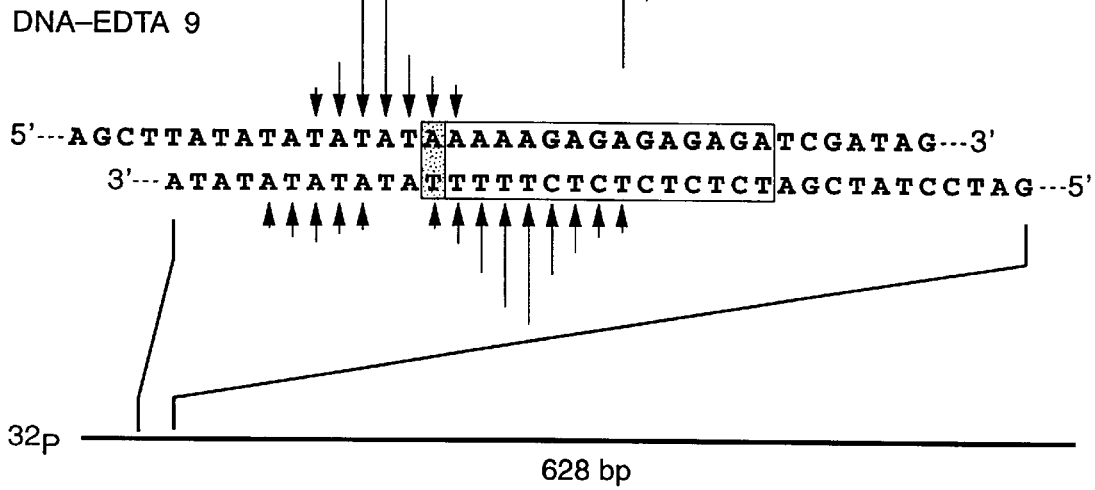
FIG._4B

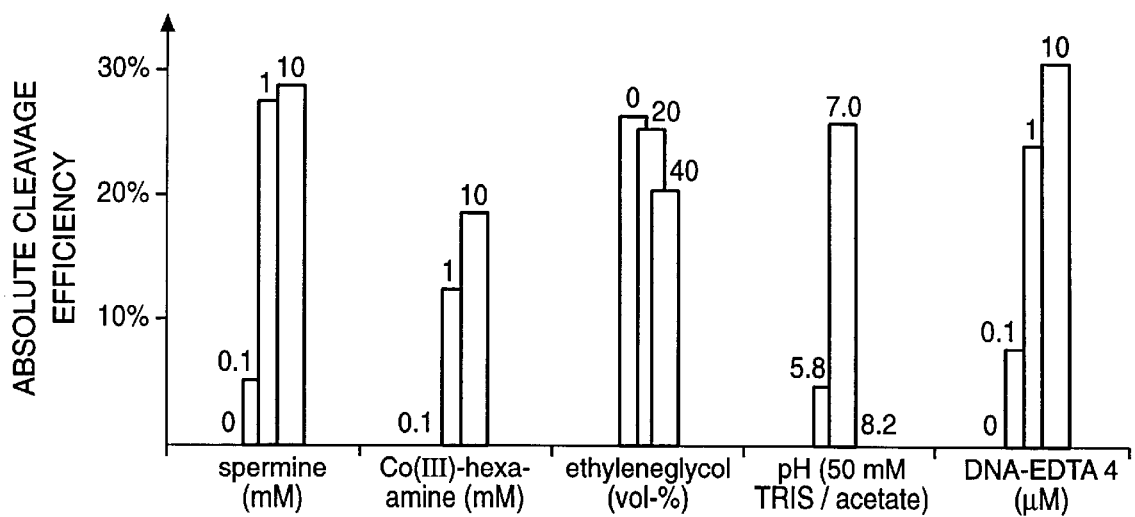
FIG._5A
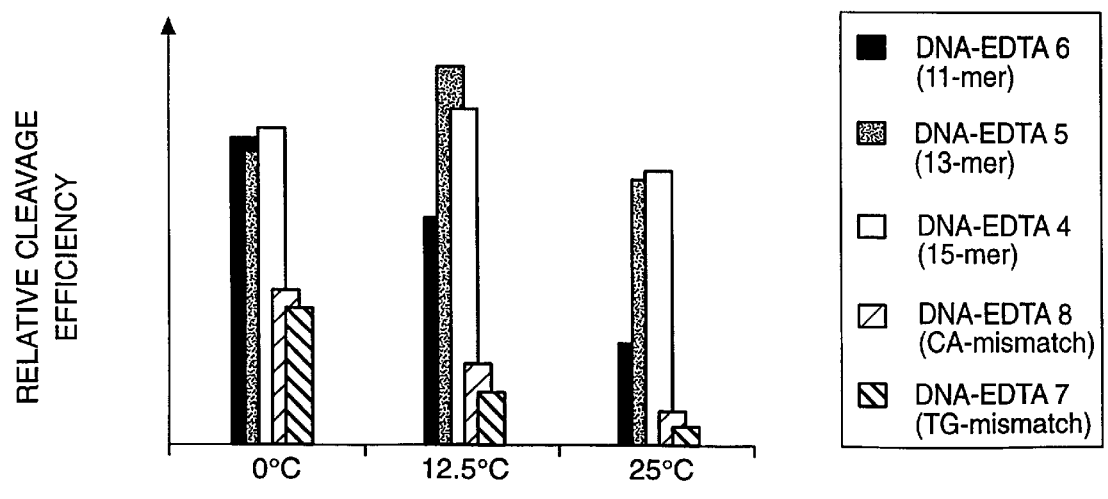
FIG._5B

TRIPLE HELIX RECOGNITION OF DNA

The instant application is a continuation application of Ser. No. 08/152,250, filed Nov. 12, 1993, now U.S. Pat. No. 5,789,155, which is a continuation of Ser. No. 07/614,205, filed Nov. 16, 1990, now abandoned, which is a divisional application of Ser. No. 07/115,922, filed Oct. 30, 1987, now abandoned.

The U.S. Government has certain rights in this invention pursuant to Grant No. NN00014-88-K-0441 awarded by the Department of the Navy and Grant No. GM 35724-13.

FIELD OF THE INVENTION

This invention relates to nucleic acid probes for sequence-specific recognition and cleavage of double-helical nucleic acids through the intermediacy of a triple-helix.

BACKGROUND OF THE INVENTION

The sequence-specific cleavage of double-helical deoxyribonucleic acid (hereafter "DNA") by naturally occurring restriction endonucleases is essential for many techniques in molecular biology including gene isolation, DNA sequence determinations chromosome analysis, gene isolation and recombinant DNA manipulations. Other applications include diagnostic reagents to detect pathogens and aberrant DNA molecules as well as chemotherapeutics.

The usefulness of DNA cleavage by these naturally recurring restriction enzymes is limited. The binding site sizes of naturally occurring restriction enzymes are typically in the range of four to eight base pairs, and hence their sequence specificities may be inadequate for mapping genomes ($10^5$–$10^7$ base pairs) over very large distances. For unique recognition of DNA in the $10^5$–$10^7$ base pair range, sequence specificities at the 8–15 base pair level must be obtained. In addition, there are a limited number of known restriction endonucleases. Thus, they cannot be used to specifically recognize a particular piece of DNA (or RNA) unless that piece of DNA contains the specific nucleic acid sequences recognized by the endonucleases.

With the advent of pulsed field gel eloctrophoresis, separation of large (up to at least one million base pair) pieces of DNA is now possible. The design and synthesis of sequence-specific DNA recognition and cleaving molecules that go beyond the specificities of the natural restriction enzymes is obviously desirable, as they would provide valuable tools for further research, diagnostics, and chemotherapeutics.

Synthetic sequence-specific binding moieties for double-helical DNA that have been studied are typically coupled analogs of natural products (P. D. Dervan, *Science* 232, 464 (1986)), transition metal complexes (J. K. Barton, *Science* 233, 727 (1986)), and peptide fragments derived from DNA binding proteins (J. Sluka, et al., *Science*, in press). Additionally, methidium-propyl-EDTA (hereafter "MPE"), which contains the metal chelator ethylenediaminetetraacetic acid ("EDTA") attached to the DNA intercalator methidium, has been shown to cleave double-helical DNA efficiently in a reaction dependent on ferrous iron (Fe(II)) and dioxygen ($O_2$). This mechanism is thought to occur by binding in the minor groove of the right-handed DNA helix. Addition of reducing agents such as dithiothreitol (hereafter "DTT") increases the efficiency of DNA cleavage, as reported by Hertzberg and Dervan, *J. Am. Chem. Soc.* 104, 313–315 (1982); and Hertzberg and Dervan, *Biochemistry*. supra). MPE-Fe(II) cleaves DNA in a relatively non-sequence specific manner, and with significantly lower sequence specificity than the enzyme DNAseI, and therefore is useful in experiments to identify binding locations of small molecules such as antibiotics, other drugs, and proteins on DNA, Hertzberg and Dervan, *Biochemistry*, supra.

The most sequence-specific molecules characterized so far, with regard to the natural product analog approach is bis(EDTA-distamycin) fumaramide which binds in the minor grove and cleaves at sites containing nine base-pair (hereafter "bp") of contiguous A,T DNA (Youngquist and Dervan, *J. Am. Chem. Soc.* 107, 5528 (1985)). A synthetic peptide containing 52 residues from the DNA binding domain of Hin protein with EDTA at the amino-terminus binds and cleaves at the 13 bp Hin site (Bruist, et al., *Science* 235, 777 (1987); Sluka, et al., supra). Another known DNA cleaving function involves the attachment of a DNA-cleaving moiety such as a ethylenediaminetetraacetic acid-iron complex (hereafter "EDTA-Fe(II)"), to a DNA binding molecule which cleaves the DNA backbone by oxidation of the deoxyribose with a short-lived diffusible hydroxyl radical (Hertzberg and Dervan, *Biochemistry* 23, 3934 (1984)). The fact that the hydroxyl radical is a relatively non-specific cleaving species is useful when studying recognition, because the cleavage specificity is due to the binding moiety alone, not some combination of cleavage specificity superimposed on binding specificity.

Despite this progress, the current understanding of molecular recognition of DNA is still sufficiently primitive that the elucidation of chemical principles involved in creating specificity in sequence recognition at the $\geq 15$ base pair level has been slow in development in comparison to the interest in the field for mapping large genomes.

Recognition of single-stranded nucleic acids by nucleic acid-hybridization probes consisting of sequences of DNA or RNA are well known in the art. Typically, to construct a DNA hybridization probe, selected target DNA is obtained as a single-strand and copies of a portion of the strand are synthesized in the laboratory and labeled using radioactive isotopes, fluorescing molecules, photolytic dyes or enzymes that react with a substrate to produce a color change. When exposed to complementary strands of target DNA, the labeled DNA probe binds to (hybridizes) its complementary single-stranded DNA sequence. The label on the probe is then detected and the DNA of interest is thus located. Probes may similarly be used to target RNA sequences. DNA probes are currently well known in the art for locating and selecting genes of known sequence, and in the diagnosis and chemotherapy of genetic disorders and diseases.

Oligonucleotides (polynucleotides containing between 10 and 50 bases) equipped with a DNA cleaving moiety have been described which produce sequence-specific cleavage of single-stranded DNA. Examples of such moieties include oligonucleotide-EDTA-Fe hybridization probes ("DNA-EDTA") which cleaves the complementary single strand sequence (Dreyer and Dervan, *Proc. Natl. Acad. Sci. USA*. 82, 968 (1985); Chu and Orgel, *Proc. Natl. Acad. Sci. USA*. 82, 963 (1985)). Such probes are disclosed in the co-pending U.S. Patent Application of Dervan et al., "Nucleic Acid Probes And Method For Using Same," Ser. No. 695,082, filed Jan. 25, 1985, and assigned to the same assignee as the present application.

In addition to double and single-stranded configurations, it is also well known in the art that triplexes of nucleic acids naturally exist (Howard, et al., *Biochem. BioPhys. Res. Commun.* 17, 93 (1964)). Poly(U) and poly(A) were found to form a stable 2:1 complex in the presence of $MgCl_2$. After this, several triple-stranded structures were discovered (Michelson, et al., *Proc. Nucl. Acid Res. Mol. Biol.* 6, 83

(1967); Felsenfeld and Miles, *Annu. Rev. Biochem.* 36, 407 (1967)). Poly(C) forms a triple-stranded complex at pH 6.2 with guanineoligoribonucleotides. One of the pyrimidine strands is apparently in the protonated form (Howard, et al., supra). In principle, isomorphous base triplets (T-A-T and C-G-C$^+$) can be formed between any homopyrimidine-homopurine duplex and a corresponding homopyrimidine strand (Miller and Sobell, *Proc. Natl. Acad. Sci. U.S.A.* 55, 1201 (1966); Morgan and Wells, *J. Mol. Biol.* 37, 63 (1968); Lee et al., *Nucleic Acids Res.* 6, 3073 (1979)). The DNA-duplex poly(dT-dC)-poly(dG-dA) associates with poly(U-C) or poly(dT-dC) below pH 6 in the presence of $MgCl_2$ to afford a triple-stranded complex. Several investigators have proposed an anti-parallel orientation of the two polypyrimidine strands based on an anti conformation of the bases, ibid. X-ray detraction patterns of triple-stranded fibers (poly(A)-2poly(U) and poly(dA)-2poly(dT)) supports this hypothesis (Arnott and Bond, *Nature New Biology* 244, 99 1973); Arnott and Selsing, *J. Mol. Biol.* 85, 509 (1974); and Arnott et al., *Nucleic Acids Res.* 3, 2459 (1976)), and suggested an A'-RNA-like conformation of the two Watson-Crick base paired strands with the third strand in the same conformation, bound parallel to the homopurine strand of the duplex by Hoogsteen-hydrogen bonds. (Hoogsteen, *Acta Cryst.* 12, 822 (1959)). The twelve-fold helix with dislocation of the axis by almost three angstroms, the C3'-endo sugar puckering and small base-tilts result in a large and deep major groove that is capable of accommodating the third strand (Saenger, *Principles Of Nucleic Acid Structure*, edited by C. R. Cantor, Springer-Verlag, New York, Inc. (1984). A high resolution X-ray structure of a triple-helical DNA or RNA is not known in the art. Importantly, there are no techniques described in the literature for determining whether a specific homopyrimidine-homopurine tract (e.g. 15 bp) within a large duplex DNA (e.g. >$10^3$ bp can form a triple helix as a method of recognition at that site.

No analytical or recombinant DNA applications of triple-helical DNA or RNA have been reported. Although triple-stranded structures of polynucleotides were discovered decades ago, the biological significance has remained obscure. Such triplexes were proposed to be involved in processes such as regulation of gene expression, maintenance of folded chromosome conformations, chromosome condensation during mitosis, and induction of local conformational changes in B-DNA (Morgan, *Trends Biochem. Sci.* 4, N244 (1979); Hopkins, *Comments Mol. Cell Biophys.* 2, 153 (1984); Minton, *J. Exp. Path.* 2, 135 (1985)).

The above-described methods for sequence-specific DNA recognition and cleavage have been limited to single-stranded DNA hybridization probes, to natural or synthetic restriction endonucleases, and to those molecules which recognize sequences of DNA directly such as antibiotics, and DNA intercalators such as methidium.

Surprisingly, the present inventors have discovered compositions and methods of specifically tailored recognition of a significantly larger number of double-stranded DNA and RNA sites than was previously possible, utilizing triple helix formation ($\geq 15$ bp recognition) at discrete highly specific sites within large DNA. The compositions of the present invention, utilized by the methods set forth herein, will provide useful tools for chromosome analysis, gene mapping and isolation. Moreover, as molecular biology defines specific disease states at the DNA level, the present invention finds usefulness in diagnostic strategy, as well as chemotherapeutics.

DISCLOSURE OF THE INVENTION

The present invention relates to recognition of homopyrimidine-homopurine double-helical tracts within large DNA, RNA, and in DNA-RNA double-helical hybrid duplexes, by triple-helix formation under physiologic conditions. The present invention also relates to cleavage of said discrete, double-helical tracts.

One object of the present invention is to provide homopyrimidine oligonucleotides and their neutral or cationic analogs equipped with markers, lables, chemotherapeutic agents and/or efficient DNA cleaving moieties at the 5' end, which are capable of forming triple helices, which can be produced in sufficient quantities to provide pharmaceutical, laboratory, or industrial compositions useful for chromosome analysis, gene mapping and isolation, diagnostics and chemotherapeutics. An additional object of the present invention is to utilize precisely tailored polynucleotide hybridization probes adapted for automated synthesis and which afford control over the precise location in a large double-helical nucleic acid of a label or DNA cleaving moiety at any base position in the polynucleotide probe strand.

Another object of the present invention is to provide polynucleotide hybridization probes and methods for their use in the recognition of any specific sequence within a large double-helical nucleic acid. Such probes are designed and adapted as described above, with the substitution of a radioactive label, photolytic dye, enzyme, or a fluorescing, or otherwise detectable molecule for the DNA cleaving moiety.

One object of this invention is to provide a method for delivering chemotherapeutic agents in vivo that eliminates the need to denature the DNA before the agent can act. Yet another object of this invention is to provide a method for precisely locating a chemotherapeutic agent or replacement gene sequence at a specific homopyrimidine-homopurine tract anywhere in a large double-stranded nucleic acid. This invention also finds application in diagnostics for gene-based diseases, and eliminates the need for many steps in the commonly used diagnostic processes.

It is also an object of the present invention to provide a new assay for triple helices.

Additional objects and advantages of the invention will be set forth in part in the description which follows, and in part will be obvious from the description or may be learned from practice of the invention. The objects and advantages may be realized and obtained by means of the instrumentalities and combinations particularly pointed out in the appended claims.

To achieve the objects and in accordance with the purposes of the present invention, homopyrimidinepolydeoxyribonucleotide probes with at least one detectable marker, chemotherapeutic agent or a DNA-cleaving moiety attached to at least one predetermined position are set forth which are capable of binding the corresponding homopyrimidine-homopurine tracts within large double-stranded nucleic acids by triple-helix formation at a predetermined site.

The compositions and the methods of the present invention allow for cleavage of one or both strands of the Watson-Crick DNA. It is this cleavage event by bifunctional DNA-EDTA probes (i.e., recognition and cleavage) that allowed the triple helix formation at discrete locations to be mapped on large DNA using gel electrophoresis.

The polynucleotide sequences of the invention may be either synthetic sequences or restriction fragments ("natural") DNA sequences. The compositions and methods of this invention are understood to apply equally for double-helical RNA, as well as to hybrid duplexes with one strand of DNA and one strand of RNA.

Also to achieve the objects of this invention, an assay for triple helices of up to at least 15 bp is disclosed.

Additionally, to achieve the objects and in accordance with the purposes of the present invention, a method is disclosed which results in recognition, chemotherapeutic alteration, and if desired, cleavage of homopyrimidine-homopurine tracts within a large double-stranded nucleic acid by triple helix formation at a particular, predetermined site. This method comprises:

(a) hybridizing a specific homopyrimidine-homopurine tract within a large double-stranded nucleic acid with a corresponding polynucleotide hybridization probe, said nucleotide containing at least one nucleoside to which is attached at least one of the following:
   (i) at least one detectable label molecule capable of being detected upon the binding of said nucleotide to said tract,
   (ii) at least one molecule adapted to cleave at least one strand in said homopyrimidine-homopurine tract,
   (iii) at least one molecule of a chemotherapeutic agent;

(b) permitting said hybridization to proceed to formation of a triple-helix; and (c) at least one of the following:
   (i) detecting said label;
   (ii) cleaving one or both strands of the nucleic acid; or
   (iii) permitting said chemotherapeutic agent to act.

It is understood that both the foregoing general description and the following detailed description are exemplary and explanatory only and are not restrictive of the invention as claimed.

The accompanying drawings, which are incorporated in and constitute a part of the specification, illustrate some embodiments of the invention and, together with the description, serve to explain the principles of the invention.

BRIEF DESCRIPTION OF THE DRAWINGS

FIG. 1 depicts the bonding of two Watson-Crick base pairs, and also the bonding of isomorphous base triplets of TAT and C$^+$GC.

FIG. 2 is a schematic representation of the cleavage of double-helical DNA by a triple-helix-forming DNA-EDTA-Fe probe, and the generation of a localized hydroxyl radical.

FIG. 3A is an autoradiogram showing the cleavage products of a double-stranded DNA containing (dA-dT)$_{15}$ after exposure to DNA-EDTA probes 1–3 as analyzed by Maxam-Gilbert sequencing methods.

FIG. 3B shows the nucleotide sequence of. DNA-EDTA probes 1–3. This Figure also presents histograms of the DNA cleavage patterns derived by densitometry of the autoradiogram of FIG. 3A (lanes 3–5 and 8–10).

FIG. 4A is an autoradiogram showing the cleavage products of a 628 bp EcoRI/BgII restriction fragment of plasmid pDMAG10 after exposure to DNA-EDTA probes 4–9, as analyzed by Maxam-Gilbert sequencing methods.

FIG. 4B shows the nucleotide sequence of DNA-EDTA probes 4–9. This figure also represents histograms of the DNA cleavage patterns derived by densitometry of the autoradiogram of FIG. 4A from the cleavage of the restriction fragment with DNA-EDTA probes 4 and 9.

FIG. 5(A) is a bar graph presenting the absolute cleavage efficiencies obtained with DNA-EDTA probe 4 under various conditions.

FIG. 5(B) is a bar graph presenting relative cleavage efrficiencies obtained with DNA-EDTA probes 4–8 at three temperatures.

FIG. 6A is an autoradiogram showing the cleavage products of plasmid pDMAG10 after exposure to DNA-EDTA probe 9 under various conditions, as analyzed on a nondenaturing agarose gel.

FIG. 6B (left) is a schematic representation of the course resolution cleavage pattern from FIG. 6A. FIG. 6B (middle) is a simplified schematic model depicting a triple helix complex with the Hoogsteen bound DNA-EDTA probe 9 at one unique site within plasmid pDMAG10 DNA.

BEST MODES FOR CARRYING OUT THE INVENTION

Reference will now be made in detail to the presently preferred embodiments of the invention, which, together with the drawings and the following examples, serve to explain the principles of the invention.

FIG. 1 shows typical binding of base pairs and triplets as referred to herein. Structure 1 of FIG. 1 shows a standard representation of Watson-Crick base pairing of nucleotide bases A (adenine) and T (thymine). Major groove 2 and minor groove 3 are shown where they would appear in an A-helical structure; B-helical structures (not shown) are also encompassed within the scope of this invention.

Structure 4 of FIG. 1 shows Watson-Crick base pairing of G (guanine) and C (cytosine). Major groove 5 and minor groove 6 are indicated.

Structure 7 of FIG. 1 shows isomorphous base triplets of TAT; the additional pyrimidine strand is bound by Hoogsteen-hydrogen bonds in the major groove to the complementary purine strand shown in Watson-Crick duplex 1.

Structure 8 of FIG. 1 shows isomorphous base triplets of C$^+$GC. The additional pyrimidine is bound as described above.

As described generally above, the polynucleotide hybridization probes of the present invention are designed to be used to detect specific nucleic acid sequences within large double helical nucleic acids through the formation of triple-helices.

Construction of hybridization probes for recognition of single-stranded nucleic acids, consisting of sequences of deoxyribonuceotides (DNA) or ribonucleotides (RNA) are well-known in the art. Typically, to construct a hybridization probe, selected target double-stranded DNA or RNA is obtained as a single strand and copies of a portion of the strand are synthesized in the laboratory and labeled using radioactive isotopes, fluorescing molecules, or enzymes that react with a substrate to produce color change. When exposed to complementary strands of target DNA, for example in a sample of tissue fluid taken from a patient, the labeled DNA or RNA probe binds to (hybridizes) its complementary single-stranded sequence. The label on the probe is then detected and the sequence of interest is thus located. Probes constructed of RNA sequences may be used to hybridize with a single complementary strand of double-helical DNA forming heteroduplexes without necessitating denaturating of the double-helical DNA (Thomas, et al., *Proc. Natl. Acad. Soc. USA*, 73, 2294–2298 (1976)).

The hybridization probes as used in the practice of this invention are unique In that they hybridize with double-stranded helices. They form a true triple helix, not a D-loop nor other triple-stranded structure.

The probes of the present invention may be constructed complementary to a fragment of a natural sequence, i.e., a fragment of a polynucleotide which occurred in nature, or which has been cloned and expressed in the laboratory. Additionally, the polynucleotide probes of the present invention may be synthetically created, by hand or with automated apparatus. It is believed that the means for synthetic creation of polynucleotide sequences are generally known to one of ordinary skill in the art, particularly in light of the teachings herein; see, e.g., Horvath, et al., *Methods In Enzymology* 154, 313–326 (1987). Because the probe can contain any predetermined complementary nucleotide sequence, it is specifically targetable and can deliver a marker or label, chemotherapeutic agent or cleavage moiety to the exact site desired in a specific homopyrimidine-homopurine tract within even a very large double-stranded nucleic acid.

In one embodiment of this invention, a polynucleotide hybridization probe is tethered to a metal chelator for cleaving a specific nucleic acid sequence. For example, FIG. 2 depicts oligonucleotide-directed cleavage of double-helical DNA by a triple-helix forming DNA-EDTA-Fe probe. One thymidine has been replaced by thymidine with the iron chelator EDTA covalently attached at C-5. Reduction of dioxygegn generates a localized hydroxyl radical at this point.

DNA and RNA hybridization probes are selected, or constructed, to be complementary to any target DNA or RNA. Thus, the label, chemotherapeutic agent, or cleavage moiety of the present invention may be incorporated along the length of any such probe so as to provide precisely the major groove cleavage desired by the practitioner. Also, more than one label, agent or moiety may be included in the probe. Previously known and familiar-hybridization sequences can be assembled, even by currently available automated technology, incorporating the label, agent, or cleavage moiety of the present invention. Therefore, the choice of probes would not require undue experimentation. The probes of this invention can be of any operable length, with a preferred range being between fifteen and three billion nucleosides. The present invention offers the flexibility, precision, and efficiency long needed in the art.

In a preferred embodiment, a nucleic acid-cleaving moiety, such as a metal chelator, is attached to a nucleoside base during synthesis of a novel nucleoside and the so-modified nucleoside is then incorporated into a selected polynucleotide using standard procedures. This polynucleotide containing the chelator-modified nucleoside recognizes the corresponding complementary sequence of double-helical homopyrimidine-homopurine DNA for which a probe is desired. Alternatively, the metal chelator may be attached to a selected nucleotide located within a given polynucleotide sequence. In the presence of dioxygen ($O_2$), an appropriate metal ion, and a reducing agent, the DNA-chelator probe yields a strand break at the target complementary DNA sequence, cleaving one or both strands at that site.

Oligonucleotides equipped with a DNA cleaving moiety have been described which produce sequence-specific cleavage of single-stranded DNA, supra. Examples of such moieties include oligonucleotide-EDTA-Fe hybridization probes (DNA-EDTA) which cleave a complementary single strand sequence (Dreyer and Dervan, *Proc. Natl. Acad. Sci. USA* 82, 968 (1965); and Chu and Orgel, *Proc. Natl. Acad. Sci. USA* 82, 963 (1965)). One example of a DNA-EDTA probe is synthesized using a novel nucleoside, 5'-DMT-T*-triethylester derived from deoxyuridine to which is attached the metal chelator EDTA as described in detail in the co-pending application mentioned above. Such probes are also described in Dreyer and Dervan, *Proc. Natl. Acad. Sci. USA*, supra. These references disclose an EDTA-nucleoside composition Incorporated into a 19-nucleotide base pair sequence of DNA complementary to a 19 bp sequence in a 167 bp restriction fragment of DNA from the plasmid pBR322. This DNA-EDTA probe was then used in the presence of the metal ion Fe(II), atmospheric dioxygen, and the reducing agent dithiothreitol (DTT) to afford specific cleavage at its complementary 9 bp complement in single-stranded plasmid DNA.

Chelators or other cleavage moieties, as well as marker labels and chemotherapeutic agents may be incorporated into the polynucleotide sequences of the probes of the present invention at various positions for which the chemistry for attachment at such positions is known, provided that such attachment is accomplished so as not to disrupt the hydrogen-base pair bonding between the DNA or RNA sequences during hybridization of the probes.

A labeled, cleavage- or otherwise-adapted nucleoside may be incorporated into the polynucleotide sequence of a probe chemically using known oligonucleotide synthesis methodology, or enzymatic procedures well known in the art.

The probes may be labeled in various well known ways for detection and diagnostic applications, for example with radioactive metal such as $^{99}$Tc following the procedures of D. R. Elmalch, et al., *Proc. Natl. Acad. Sci.* 81, 918 (1984) and EDTA or with fluorescent elements such as the lanthanides $Tb^{+3}$ or $Eu^{+3}$. Leung, et al., *Biochem. Biophys. Res. Comm.* 75, 15 (1977). If a chelator is desired to be used in a cleavage moiety, other metal chelators may be used in place of EDTA such as polyamines or other chelators capable of binding Fe(II–III) or Cu(I–II). Other polyamino carboxylic metal chelators way be utilized in place of EDTA such as 1,2-diamino-cyclohexane tetraacetic acid, diethylenetriamine pentaacetic acid, ethylenediamine di-(-O-hydroxyphenol-acetic acid), and hydroxyethylene diamine triacetic acid. A metal chelator may be attached to the nucleotide probe during synthesis via a hydrocarbon-amide linkage which may consist of several carbon atoms. The specificity of the probe for the reaction site is prescribed by the nucleotide sequence within which the metal chelator or other cleavage moiety is attached. The moiety can be incorporated into polydeoxyribonucleotides or polyribonucleotides of any desired length and sequenced using routine phosphoramidite or phosphotriester procedures.

One convenient synthesis of DNA-EDTA probes involves the incorporation of a modified thymidine into an oligonucleotide by chemical methods. This approach allows for automated synthesis and affords control over the precise location of the EDTA moiety at any thymidine position in the oligonucleotide strand, Felsenfeld, et al., supra. Homopyrmidine oligonucleotides and their neutral or cationic analogs may also be used in this invention. In the examples which follow, oligonucleotides-EDTA probes of different length, composition, and EDTA-thymidine position were synthesized in this manner. Each of the DNA-EDTA probes described in the Examples was purified by gel electrophoresis.

In a preferred embodiment of this invention, bifunctional DNA-EDTA probes are used for recognition and cleaving of the target double-stranded nucleic acid. These probes allow triple helix formation at a discrete location to be mapped on large DNA using gel electrophoresis. An important part of the present invention involves the development of preferred assay conditions for measuring formation and cleavage of the triple helix. This will be discussed in more detail in Example 2 below. However, the preferred general conditions for the cleavage reactions are as follows: approximately 100 nM in bp radio labeled restriction fragment (approximately 10,000 cpm), 25 nM tris/acetate, pH 7.0, 1 nM spermine, (MY), 100 nM NaCl, 100 μmolar in vp sonicated, deproteinized cath-thimus DNA, 20 volume-percent ethyleneglycol, 1 μmolar DNA-EDTA probe, 25 μmolar Fe(II) and 2 nM DTT. The cleavage reactions were run for approximately 16 hours at 0–25° C. These conditions may be varied without departing from the scope of this invention.

As described in the examples below, the affinity cleaving method utilizing DNA, EDTA and known In the art allows the effect of reaction conditions, probe length, and single base mismatches on triple-helix formation to be analyzed on high resolution sequencing gels. Precise methods for quantitation and measurement and determination of the presence and orientation of triple helices is set out in more detail in the Examples below.

As will be seen in the Examples, the directional orientation of the third strand as well as the identity of the grooves in right-handed DNA-helix occupied by the bound DNA-EDTA probe can be analyzed by high resolution gel electrophoresis (FIG. 2). Additionally, the location of triple helices within large pieces of DNA can be mapped by double strand breaks analyzed by nondenaturing agarose gel electrophoresis.

Practice of this invention includes several processes: a process for identifying and recognizing formation of triple helices at a discrete highly specific site, a process for cleaving double-stranded DNA through the formation of a triple helix, and processes for diagnostic and chemotherapeutic use of the triple helices of this invention.

Additionally, to achieve the objects and in accordance with the purposes of the present invention, a process is disclosed which results in recognition, chemotherapeutic use, and if desired, cleavage of homopyrimidine-homopurine tracts within a large double-stranded nucleic acid by triple helix formation at a particular, predetermined site. This method comprises:

(a) hybridizing a specific homopyrimidine-homopurine tract within a large double-stranded nucleic acid with a corresponding polynucleotide hybridization probe, said nucleotide containing at least one nucleoside to which is attached at least one of the following:
  (i) at least one detectable label molecule capable of being detected upon the binding of said nucleotide to said tract,
  (ii) at least one molecule adapted to cleave at least one strand in said homopyrimidine-homopurine tract,
  (iii) at least one molecule of a chemotherapeutic agent;
(b) permitting said hybridization to proceed to formation of a triple-helix: and
(c) at least one of the following:
  (i) detecting said label;
  (ii) cleaving one or both strands of the nucleic acid; or
  (iii) permitting said chemotherapeutic agent to act.

More details on the methods for recognition and cleavage are set forth in the Examples.

Synthesis and the preparation of necessary and desired component parts of the probes of the present invention, and their assembly is believed to be within the duties and tasks performed by those with ordinary skill in the art and, as such, are capable of being performed without undue experimentation.

The probes described in this invention generally range in length from 11 to 15 bases. This size increase relative to restriction endonucleases permits sequence recognition orders of magnitude greater than that possible with restriction endonucleases. From the disclosure and Examples herein, it is clear that larger, as well as smaller, probes would work in similar fashion as disclosed herein.

The probes of the present invention are not limited to the production of sequence-specific cleavage of double-stranded DNA by triple-helix formation, but may also be utilized as diagnostic agents when a radioisotope labeled, fluorescing, or otherwise detectable metal ion is attached to the probe. The probes of the present invention may also be used as target-specific chemotherapeutics with the attachment of an "artificial" or natural gene repressor or other effective agent to the polynucleotide.

It is to be understood that various other modifications will be apparent to and can readily be made by those skilled in the art, given the disclosure herein, without departing from the scope and spirit of this invention. Accordingly, it is not intended that the scope of the claims appended hereto be limited to the description as set forth herein, but rather that the claims be construed as encompassing all the features of patentable novelty which reside in the present invention, including all features which would be treated as equivalents thereof by those skilled in the art to which this invention pertains.

Examples of the application of the probes of the present invention, and representative protocols and processes for their use appear below.

INDUSTRIAL APPLICABILITY

This invention finds usefulness in a range of medical and laboratory applications. It greatly enhances current capabilities for recognition of a small homopyrimidine-homopurine tract in a large double-helical nucleic acid without requiring denaturation of the double-helix or its digestion into smaller pieces before the identification. The probes of the current invention and the method for their use could become useful tools in chromosome analysis, gene mapping and isolation, as well as other laboratory procedures. Moreover, as molecular biology defines specific disease states at the DNA level, a chemotherapeutic strategy of "artificial repressors" based on triple-helix-forming nucleic acid analogs becomes a possibility.

EXAMPLES

For the following examples, nine homopyrimidine DNA probes, 11–15 nucleotides in length, described in more detail below, each containing a single thymidine with EDTA covalently attached at C-5 (labeled T*), were synthesized for binding and cleavage studies with two different duplexed target DNA's.

Generally, unless specifically controverted below, the following definitions apply: DMT refers to 4,4-dimethoxytrityl; DTT refers to dithiothreitol; DNA-EDTA 1–9, the probes examined below, refers to oligodeoxyribonucleotides with an EDTA-modified thymidine at positions 1, 5, or 8; Spermine indicates spermine-4-HCl (Aldrich, 98% pure) which was dissolved in water and then pH adjusted with NaOH to 7.4; TBE-buffer includes 0.89 nM TRIS (meaning TRIS(hydroxy-methyl)aminomethane), 0.89 mM Boric acid, and 1 mM EDTA-disodium salt; Fe(II) refers to $Fe(NH_4)_2(SO_4)_2 \cdot 6H_2O$. Aqueous solutions of DTT and Fe(II) were freshly prepared before use.

Example 1

Determination of Orientation and Groove Location of Hoogsteen Strand Binding Watson-Crick DNA Although it is widely believed that the two homopyrimidine strands in triple-helical DNA or RNA are antiparallel a definite proof is lacking in the published literature. A double-stranded DNA was examined that contains (dA-dT)$_{15}$ as a target sequence which could, in principle, bind the d(T)$_{15}$ probe-strand in parallel or antiparallel orientation. A 30-base pair duplex of DNA containing the tract (dA-dT)$_{15}$ was labeled separately at the 5' end of each strand. This was allowed to incubate with (T)$_{15}$-EDTA probes 1 to 3 (shown in FIG. 3B) with the thymidine-EDTA located at oligonucleotide positions 8, 5, and 1, from the 5'-end, respectively. The $^{32}$P-labeled DNA was dissolved in buffer containing calf-thymus DNA, NaCl, TRIS, spermine and ethylene glycol and was mixed with the DNA-EDTA-Fe(II) probes, previously equilibrated with Fe(II) for 1 minute. After incubation at 0° C. for 10 minutes, the reactions were initiated by addition of an aqueous solution of DTT, such that the final concentrations were 10 mM TRIS/HCl (pH 7.4), 1 mM spermine, 100 mM NaCl, 40 vol-% ethylene glycol, 100 μM (bp) of calfthymus DNA, 0.67 pM DNA-EDTA probe, 25 μM Fe(II) and 1 mM DTT(33). The cleavage reactions were allowed to proceed for 15 hours at 0° C. and then stopped by freezing and lyophilization. The resulting cleavage products were separated by electrophoresis on a denaturing 20 percent polyacrylamide gel and visualized by autoradiography (FIG. 3A).

FIG. 3A shows an autoradiogram of the 20 percent Maxam-Gilbert sequencing gel. Lanes 1 to 5 contain 5'End-labeled d(A$_5$T$_{15}$G$_{10}$); lanes 6 to 10 contain 5'-End-labeled d(C$_{10}$A$_{15}$T$_5$). The Maxam-Gilbert G+A sequencing reactions used for lanes 1 and 6 are disclosed in Maniatis et al., *Molecular Cloning, A Laboratory Manual*, Cold Spring Harbor Laboratory (1982), and Maxam and Gilbert, *Methods Enzymol.* 65, 499 (1987). Controls in lanes 2 and 7 showing the two 5'-labeled 30-bp DNA standards were obtained by treatment according to the cleavage reactions In the absence of DN-EDTA-Fe probes. Lanes 3 to 5 and 8 to 10 are the DNA cleavage products in the presence of DNA-EDTA-Fe probes 1 to 3, approximately 0.5 μM (bp) 5'-$^{32}$P-labeled DNA, (approximately 10,000 cpm), 10 mM TRIS/HCl, pH 7.4, 1 mM spermine, 100 mM NaCl, 100 μM (bp) sonicated, deproteinized calfthymus DNA, 40 percent by volume ethylene glycol, 0.67 μM probe, 25 μM Fe(II) and 1 mM DTT; incubated for 15 hours at 0° C. Lanes 3 and 8 contain DNA-EDTA-Fe 1, lanes 4 and 9 contain DNA-ET-Fe 2, lanes 5 and 10 are DNA-EDTA-Fe 3.

On the d(T)$_{15}$ strand of the Watson-Crick duplex, one major cleavage site is observed for each DNA-EDTA probe 1–3 with the maximum cleavage site shifted to the 5'-side of T*. The location of the cleavage patterns on Watson-Crick DNA produced by the probes 1–3 with respect to the position of T* reveal the orientation of the DNA-EDTA probe on the duplex DNA (FIG. 3B).

FIG. 3B shows the (T)$_{15}$-EDTA probes 1–3 where T* is the position of the thymidine-EDTA. Also shown are histograms of the DNA cleavage patterns for these probes, derived by densitometry of the autoradiogram shown in FIG. 3A (lanes 3–5 and 8–10). The heights of the arrows represent the relative cleavage intensities at the indicated bases. Arrows are shown if the cleavage intensity at a particular nucleotide was greater than 5% when compared to that of the nucleotide cleaved the most efficiently. The box in each histogram indicates the double-stranded sequence which is bound by the DNA-EDTA-Fe(II) probes 1–3. The Watson-Crick base-pair to which T* is Hoogsteen hydrogen bonded in the triple-strand helix is shaded.

As seen from the orientations, the homopyrimidine-EDTA strand binds parallel to the homopurine and anti-parallel to the homopyrimidine strands of Watson-Crick DNA. These observations rule out strand displacement (D-loop) as the mode of binding. The asymmetry of the cleavage patterns on opposite strands of DNA reveals the identity of the groove in right handed DNA occupied by EDTA-Fe. An asymmetric cleavage pattern with maximal cleavage shifted to the 5' or 3' side on opposite strands corresponds to the diffusible hydroxyl radical being generated in the major or minor groove, respectively. The cleavage patterns shown in FIG. 3B reveal that the DNA-EDTA-Fe(II) probe is located in the major groove of the Watson-Crick DNA.

Homopyrimidine probes 1 and 2 which bear the EDTA at an internal base position cleave exclusively the homopyrimidine strand of the target DNA. A model of the triple-helix between these homopyrimidine-EDTA-Fe(II) probes and the double-helical DNA (not shown) reveals that the homopurine Watson-Crick strand in the triple-helix is protected from the hydroxyl radical by the sugar-phosphate backbones of the Hoogsteen-paired strand. In effect there are now three grooves in the triple helix and EDTA-Fe is exposed to only one groove (FIG. 1). The nucleotides 3 to 4 bases on the 5'-side of T* in the right-handed triple helix are proximal to the EDTA-Fe(II) and are therefore expected to be cleaved most efficiently. DNA-EDTA-Fe(II)3, which carries the cleaving moiety at the 5'-end, should form a triplex with no flanking nucleotides on the 5'-side of T*. A homopyrimidine probe with the cleaving function at the 5'-end should generate cleavage on both strands. Indeed, the d(T)$_{15}$-EDTA-Fe(II)3, carrying the ETA at the 5' end, cleaves both strands of the target duplex DNA (FIG. 3B).

Example 2

Specific Cleavage of a DNA Restriction Fragment and Determination of Assay Conditions This example illustrates two important aspects of the present invention. In the first part, it is shown that an unsymmetrical mixed probe can go into and be precisely located within any large target homopyrimidine-homopurine tract, for example a target sized a factor of 50 over the probe. In this example, restriction fragments with mixed bases are used which vary in length, have single mismatches with the known target, and vary in the positions of the EDTA (FIG. 4B).

In the second part preferred assay conditions are determined, as well as the effect of varying those conditions with probes of 11–15 bp in length.

Specific Cleavage Of A DNA Restriction Fragment

Cleavage by triple helix formation with DNA-EDTA-Fe (II) probes 4–9 was examined on a restriction fragment 628 base pairs in length that contained the sequence d(AAAAAGAGAGAGAGA). This sequence was obtained from plasmid pDMAG10 which was a gift from D. Mendel, who constructed it by inserting the d(AAAAAGAGAGAGAGA) containing duplex in the large BamHI-HindIII restriction fragment of pBR322 (Mendel and Dervan, *Proc.Natl. Acad. Sci. USA.*, 84, 910 (1987)). A single site labeled 628 bp EcoRI-BglII restriction fragment containing the target sequence was obtained by linearizing pDMAG10 with EcoRI, labeling with $^{32}$P (Van Dyke and Dervan, *Science*, 225, 1122 (1984)), and cleaving with BglI. This sequence represents a mixed homopurine target which is located 47 nucleotides from the 3'-(and 5')$^{32}$P-label of the DNA fragment. The concentration of the single stranded oligodeoxynucleotides were determined using the following epsilon values (260 mm) for each base: 15400(A), 11700 (G), 7300(C) and 8800(T).

FIG. 4A shows an autoradiogram of the 8 percent Maxam-Gilbert high-resolution polyacrylamide sequencing gel run on probes 4–9. The EcoRI/BgII restriction fragment of plasmid pDMAG10 is labeled at the 3' end with $^{32}$P. The Maxam-Gilbert G+A sequencing reactions described in the previous example were used here for lane 20. In general, the cleavage reactions were carried out as follows: a mixture of DNA-EDTA probe (1 μM) and Fe(II) (25 μM) was combined with the $^{32}$P-labeled restriction fragment (approximately 100 μM (bp)) in a solution of calf-thymus DNA (100 μM (bp)), NaCl (100 mM), TRIS/acetate, pH 7.4 (25 mM TRIS), spermine (1 mM) and ethyleneglycol (20 vol-%) and incubated for 10 minutes at 0° C. Cleavage reactions were initiated by addition of 2 mM DTT, proceeded 16 hours at 0° C. to 25° C., and stopped by precipitation with ethanol. The reaction products were analyzed on a high resolution polyacrylamide gel. For each lane the parameters differing from these general conditions are given below. (lane 21): Control, minus DNA-EDTA; (lanes 22, 27 and 32): 1 μM DNA-EDTA 6; (lanes 23, 28 and 33): 1 μM DNA-EDTA 5: (lanes 24, 29 and 34): 1 μM DNA-EDTA 4; (lanes 25, 30 and 35): 1 μM DNA-EDTA 7 (Hoogsteen-type TG-mismatch); (lanes 26, 31 and 36): 1 μM DNA-EDTA 8 (Hoogsteen-type CA-mismatch). The reactions were run for 16 hours at 0° C. (lanes 22 to 26), 12.5° C. (lanes 27 to 31) and 25° C. (lanes 21 and 32 to 36) respectively. Electrophoresis on a 5 percent polyacrylamide gel separated the radiolabeled 628 bp fragment from other digest products.

FIG. 4B shows the sequence of DNA-EDTA probes 4–9 where T* is the position of the thymidine-EDTA. Histograms shown in this figure of the DNA-cleavage patterns were determined by densitometry of the autoradiogram from the cleavage of the 628 bp restriction fragment with DNA-EDTA probes 4 and 9.

On the 3' end-labeled DNA-strand, carrying the homopyrimidine target sequence, DNA-EDTA-Fe(II) 4 and 9 both produce sequence specific cleavage patterns shifted to the 5' side of the T* position (FIG. 4B) consistent with major groove binding. The efficiency of the sequence specific cleavage of the DNA restriction fragment by DNA-EDTA-Fe(II) 4 is dependent on spermine and/or $Co(NH_3)_6^{3+}$-concentrations, ethylene glycol, pH and probe concentration (FIG. 5A).

The cleavage efficiency of probes 4–6 which differ in length (15, 13 and 11 nucleotides) and probes 7 and 8 which differ in sequence (each contain one Hoogsteen base mismatch in the triple helix complex) were examined under identical conditions at different temperatures. Identical cleavage patterns are observed for the DNA-EDTA-Fe(II) probes 4–8. At 0° C. probes 4–6 which differ in length but have in common T* at position 5 each produce a cleavage pattern of the same intensity. At 25° C. probe 6 which is 11 nucleotides in length cleaves the target DNA 3 times less efficiently than probes 5 or 4 which are 13 and 15 nucleotides in length, respectively. DNA-EDTA 7 and 8 which contain a single base mismatch at position 10 and 11 generate cleavage patterns of reduced intensity and is temperature sensitive. Compared to DNA-EDTA probe 4, the relative cleavage efficiency decreases for the single base mismatch probes 7 from 0.4 (at 0° C.) to 0.08 (25° C.) and 8 from 0.5 (at 0° C.) to 0.13 (25° C.) (FIG. 5B).

Optimization Of Assay Conditions

In this example, the effect of added cations, organic solvents, pH, temperature, probe length and sequence homology were studied. The results, detailed below, are summarized in FIG. 5.

FIG. 5A shows a bar graph presenting the absolute cleavage efficiencies obtained with DNA-EDTA-Fe 4 under various conditions. The values were determined by cutting out the corresponding pieces of the dried gel and measuring their radioactivity by scintillation counting. The numbers given are calculated by dividing the radioactivity of the cleavage site (sum of 5 most efficiently cleaved nucleotides) with the total radio-activity obtained from the uncleaved fragment, the cleavage site and the background, which is corrected for the background that resulted from the untreated 628 bp fragment. The remaining values were assigned by correlation of absolute with relative cleavage efficiencies determined by densitometry of the autoradiogram. FIG. 5(B) shows a bar graph presenting the relative cleavage efficiencies (sum of 6 most efficiently cleaved nucleotides) obtained with DNA-EDTA-Fe 4–8 (FIG. 4A) at three temperatures as determined by densitometry. The data is reproducible within ±10% of reported values.

Importance Of Added Cations

The importance of added cations for formation of triple-stranded DNA or RNA has been known since the discovery of those structures. To bind double-helical DNA, the DNA-EDTA-Fe(II) probe must overcome the repulsion between two anionic chains of the Watson-Crick duplex and its own negatively charged phosphodiester backbone. One way to achieve this is to use multivalent cations (Michelson, et al., *Prog. Nucl. Acid. Res. Mol. Biol.* 6, 83 (1967) and Felsenfeld and Miles, supra.). The naturally occuring polyamines and their derivatives are known to stabilize double-and triple-helical structures of nucleic acids. (Blaser and Gabbay, *Biopolymers* 6, 243 (1968)). We find preferred cleaving efficiencies for DNA-EDTA-Fe(II) 4 in the presence of mM concentrations of spermine or $Co(NH_3)_6^{3+}$. No cleavage occurs in the absence of spermine or $Co(NH_3)_6^{3+}$ which demonstrates the importance of these or similar cations for triple-helix formation (FIG. 5A). Spermine appears to be ideal for the stabilization of the triple-stranded complex with DNA-EDA-Fe(II) probes. It efficiently neutralizes the negative charges of the sugar-phosphate backbones and does not compete with the Fe(II) for the EDTA-moiety. No cleavage is observed if $MgCl_2$ or $CaCl_2$ (up to 8 mM) are substituted for spermine which could also be due to competition with Fe(II) for the metal chelator EDTA (Hertzberg and Dervan, *Biochemistry* 23, 3934 (1984).

Role Of Organic Solvents

According to x-ray fiber diffraction studies, the three strands of a triple helix occur in a A'RNA-like conformation (Arnott, et al., *Nucleic Acids Res.* 3, 2459 (1976)). A conformational transition may be necessary to allow the binding of the DNA-EDTA-Fe(II) probe. It is established that a B to A conformational change takes place on lowering the relative humidity. This transformation is dependent on the ratio of (A+T) to (G+C) and can be achieved by the addition of a variety of organic solvents to the DNA aqueous solution. The increase in organic solvent concentration should favor the B to A conformational transition and suggest that triple helices should form more readily (Saenger, *Principles of Nucleic Acid Structure*, edited by C. R. Cantor, Springer-Verlag, New York, Inc. (1984)). As a result, the cleavage due to the DNA-EDTA probe should increase correspondingly. We find that the efficiency of oligonucleotide duplex cleavage by $(T)_{15}$-EDTA-Fe(II) 1–3 is increased by a factor of 10 upon addition of ethyleneglycol (40 percent by volume). Other organic solvents such as methanol, ethanol, dioxane or DMF give rise to similar behavior. In the presence of ethylene-glycol, DNA-EDTA-Fe(II) probes provide cleavage patterns without detectable background, a result that may be due to radical scavenging by this solvent.

Curiously, the mixed T and C homopyrimidine EDTA-Fe (II) 4 demonstrates different behavior. The addition of 20 vol-% ethyleneglycol is not necessary and does not increase the cleavage efficiency as found in the $(T)_{15}$ case. One explanation for this difference is that a mixed T, C probe may have a higher affinity than the oligo T probe to the corresponding Watson-Crick target sequence due to the protonated cytosines requird to form the Hoogsteen-hydrogen bonds in the triple helix. The alternative explanation is that the target Watson-Crick sequences differ in conformation and one may be more A like than the other.

The PH-Dependence Of Cleavage Efficiency

Mixed homopyrimidine DNA-EDTA-Fe(II) 4 cleaves the target-DNA over a relatively narrow range of pH-values producing the maximum cleavage at pH 7.0 (FIG. 5A)(the pH values are not corrected for temperature or different ethyleneglycol percentage and are given for the tenfold concentrated buffer solutions at 25° C.). This behavior could be caused by two independent properties of the oligonucleotide-EDTA probes. On one hand, triplex formation requires protonation of cytosines at N-3 in the third strand to enable the Hoogsteen hydrogen bonds between DNA-EDTA-Fe(II) probes and the target Watson-Crick DNA. It was previously demonstrated that complexes of triple-helical nucleic acids, containing cytosines in the homopyrimidine strands, are stable in slightly acidic to neutral solutions and start to dissociate an increasing pH (Lipsett, *J. Biol. Chem.* 239, 1256 (1964); Morgan and Wells, *J. Mol. Biol.* 37, 63 (1969)). Therefore it seems not unreasonable that the DNA-EDTA-Fe(II) probes do not bind Watson-Crick DNA in slightly basic solutions (pH$\geq$8) and consequently do not produce cleavage under these conditions. On the other hand, studies with methidiumpropyl-EDTA-Fe Indicate that the cleavage efficiency of EDTA-Fe decreases sharply below pH 7 (Hertzberg and Dervan, supra), presumably due to either partial protonation of the EDTA and the resulting loss of Fe(II) or some pH-dependence of the cleavage reaction. Based on known EDTA cleavage chemistry, it is anticipated that at slightly acidic pH-values, DNA-EDTA-Fe(II) probes do not produce efficient cleavage. In data not shown, footprinting experiments confirm that the triple helix is forming at acidic pH values.

Influence of Probe Length, Temperature, and Sequence Homology

At 1 $\mu$M concentration the DNA-EDTA probe approaches the maximum cleavage efficiency on the 628 bp restriction fragment (FIG. 5A). We chose DNA-EDTA probes 15 nuclectides in length for our initial studies to attain reasonable binding affinities at the double-helical target sequence (Cassani and Bollum, *Biochemistry* 8, 3928 (1969); Raae and Kleppe, *Biochemistry* 17, 2939 (1978)). Having determined the preferred cleavage conditions for DNA-EDTA-Fe(II) 4, we focused on the size dependence for DNA-EDTA-Fe(II) probes to form a triple-helix complex with the Watson-Crick DNA. DNA-EDTA-Fe(II) probes 5 and 6, which are 13 and 11 nucleotides in size, produce cleavage patterns of similar intensities at 0° C., indicating that homopurine-homopyrimidIne sequences as short as 11 nucleotides can specifically bind the 628 bp restriction fragment. The influence of oligonucleotide length becomes more apparent if the cleavage reactions are allowed to proceed at higher temperatures. DNA-EDTA 4 and 5 cleave the target duplex DNA at 25° C. with approximately the same efficiency, whereas the relative intensity of the cleavage pattern produced by the shorter 6 becomes significantly weaker (FIGS. 4A, 5B).

In order to test the Importance of sequence homology for triple helix formation and cleavage, two probes, DNA-EDTA-Fe(II) 7 and 8, were synthesized that contained single base mismatches compared to DNA-EDTA-Fe(II) 4 but had in common the location of T* at position 5. When bound to the double-helical target sequence, probes 7 and 8 should give rise to one mismatched base-triplet with respect to the Hoogsteen hydrogen bonding. The mismatching bases in the probe-strands were chosen so that the corresponding tautomeric or protonated structurs of the mismatching pyrimidine base could still allow the formation of isomorphous base triplets. Compared to DNA-EDTA-Fe(II) 4, both single mismatch probes 7 and 8 generate weaker cleavage patterns at 0° C. and the difference becomes more apparent for the cleavage patterns produced at 25° C. (FIG. 5B). Probes 7 and 8 cleave the target DNA less efficiently than the corresponding homologous DNA-EDTA-Fe(II) 4. This result indicates that a single base-mismatch in a DNA-EDTA-Fe(II) probe, 15 nucleotides in length, can lowe the cleavage efficiency by at least a factor of 10. Clearly, the sequence specific recognition of large double-helical DNA by DNA-EDTA-Fe(II) probes is sensitive to single base mismatches indicating the importance of the correct homopyrimidine probe sequence for the formation of a triple-stranded complex with the target-DNA.

Example 3

Site Specific Double-Strand Cleavage of Plasmid DNA

The ability of DNA-EDTA-Fe(II) 9 to cause double strand breaks at a homopurine-homopyrimidine insert in large DNA is presented in FIG. A. This figure shows double-strand cleavage of plasmid DNA analyzed on a nondenaturing 0.9% agarose gel. The plasmid pDMAG10 (Mendel and Dervan, *Proc. Natl. Acad. Sci. USA* 84, 910 (1987)) was digested with StyI restriction endonuclease to produce a linear DNA fragment 4.06 kb in size which contains the homopurine site $d(A_5(AG)_5)$ located 1.0 kb upstream from the restriction site. This affords heterogenous overhangs and each end could be labeled separately using either a-$^{32}$P-ATP or a-$^{32}$P-TTP according to standard procedures. Lanes 1–3 of FIG. 6A shows plasmid pDMAG10 linearized with StyI and labeled at the downstream end of the restriction site with a-$^{32}$P-ATP. Lanes 4–6 show the same plasmid with the other end labeled with a-$^{32}$P-TTP.

The $^{32}$P-end-labeled DNA was allowed to incubate with DNA-EDTA-Fe(II) 9 (5 $\mu$M) for 10 minutes at 0° C. as previously described and the cleavage reaction was initiated by the addition of DTT (2 mM) and run at 0° C. for 16 hours. Cleavage conditions included $^{32}$P labeled DNA plasmid, 100mM NaCl, 1 mM spermine, 25 mM TRIS/acetate pH 7.0, 100 $\mu$M (bp) sonicated, deproteinized calf thymus DNA, 5 $\mu$M DNA-EDTA-Fe(II) 9, 25 $\mu$M Fe(II) and 2 mM DTT. Lanes 1 and 4 are controls containing no DA-EDTA-Fe(II) 9. Lanes 2 and 5 are DNA size markers obtained by digestion of StyI linearized pDMAG10 with EcoRI, PvuI, SalI (both ends labeled), and Xmn I labeled with a-$^{32}$P-TTP): 4058 (undigested DNA), 3338, 2994, 2368, 1690, 1460, 1064, and 720. Lanes 3 and 6 are DNA-EDTA-Fe(II) probe 9 at 5 $\mu$M added.

Separation of the cleavage products by agarose gel electrophoresis followed by autoradiography reveals only one major cleavage site producing two DNA fragments, 3.04 and 1.02 kb in size as determined by comparison with comigrating DNA size markers (FIG. 6A, lanes 3 and 6).

FIG. 6B (left) shows the course resolution cleavage pattern from gel 6A. FIG. 6B (middle) depicts a simplified model of the triple helix complex with the Hoogsteen bound DNA-EDTA-Fe(II) 9 at one unique site within 4.06 kb of plasmid DNA. The high resolution cleavage pattern at that site is shown in FIG. 4B.

This example demonstrates that the probes of this invention can go into a very large piece of double-stranded DNA and precisely locate a double-strand cleavage. This technique has tremendous potential for mapping chromosomes. The work reported here demonstrates that homopyrimidine-homopurine double-helical tracts can be recognized within large DNA by triple helix formation under physiological conditions.

What is claimed is:

1. A method for forming a triple helix in a cell cultured in vitro wherein said cell comprises a double-stranded nucleic acid involved in a gene-based disease caused by a virus, genetic defect, or oncogene, said method comprising the steps of:

contacting a subregion in said nucleic acid with an oligonucleotide to form a triple helix such that when said oligonucleotide binds in a parallel orientation to a first strand of said nucleic acid, said oligonucleotide comprises a T or a C+ bound to an A or a G respectively on said first strand, and wherein said oligonucleotide also contains a nucleoside to which is attached a moiety that alters the natural expression of said nucleic acid.

2. The method of claim 1, wherein said double-stranded nucleic acid comprises deoxyribonucleic acid.

3. The method of claim 1, wherein said double-stranded nucleic acid comprises ribonucleic acid.

4. The method of claim 1, wherein said double-stranded nucleic acid comprises a hybrid duplex with one strand of deoxyribonucleic acid and one strand of ribonucleic acid.

5. The method of claim 1, wherein said oligonucleotide comprises a pyrimidine-rich oligonucleotide and said double-stranded nucleic acid comprises a purine-rich subregion on one of the strands.

6. The method of claim 1, wherein said oligonucleotide comprises a purine-rich oligonucleotide and said large double-stranded nucleic acid comprises a purine-rich subregion on one of the strands.

7. The method of claim 1, wherein said large double-stranded nucleic acid is from a chromosome, a gene or other natural source.

8. The method of claim 1, wherein said large double-stranded nucleic acid comprises a nucleic acid encoding a viral protein and said oligonucleotide is capable of binding to a subregion within said nucleic acid encoding said viral protein.

9. The method of claim 1, wherein said large double-stranded nucleic acid comprises a nucleic acid encoding an oncogenic protein and said oligonucleotide is capable of binding to a subregion within said nucleic acid encoding said oncogenic protein.

10. The method of claim 1, wherein said moiety comprises a radioactive isotope.

11. The method of claim 1, wherein said moiety comprises a radioactive fluorescent molecule.

12. The method of claim 1, wherein said moiety comprises at least one enzyme that detectably reacts with a substrate.

13. The method of claim 1, wherein said moiety comprises a cleaving moiety that causes cleavage of said large double-stranded nucleic acid.

14. The method of claim 1, wherein said moiety comprises a chemotherapeutic agent.

15. The method of claim 1, wherein said oligonucleotide has a length between 11 and 15 nucleotides.

16. The method of claim 1, wherein said oligonucleotide has at least one modified nucleotide.

17. The method of claim 1, further comprising detecting said moiety as an indication of the presence of said subregion within said double-stranded nucleic acid.

18. The method of claim 13, further comprising cleaving said double-stranded region by said cleaving moiety.

19. The method of claim 14, further comprising permitting said chemotherapeutic agent to act.

20. The method of claim 14, wherein said chemotherapeutic agent is an artificial or natural gene repressor to specific site of interest in said double-stranded nucleic acid involved in a gene-based disease.

* * * * *